(12) United States Patent
Chen et al.

(10) Patent No.: US 10,665,347 B2
(45) Date of Patent: May 26, 2020

(54) METHODS FOR PREDICTING PROGNOSIS

(71) Applicant: OHIO STATE INNOVATION FOUNDATION, Columbus, OH (US)

(72) Inventors: James L. Chen, Columbus, OH (US); Chaitanya Shivade, Columbus, OH (US); David Liebner, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 640 days.

(21) Appl. No.: 14/912,961

(22) PCT Filed: Aug. 20, 2014

(86) PCT No.: PCT/US2014/051907
§ 371 (c)(1),
(2) Date: Feb. 19, 2016

(87) PCT Pub. No.: WO2015/026953
PCT Pub. Date: Feb. 26, 2015

(65) Prior Publication Data
US 2016/0203287 A1  Jul. 14, 2016

Related U.S. Application Data (60) Provisional application No. 61/867,767, filed on Aug. 20, 2013.

(51) Int. Cl.
*G16H 50/30* (2018.01)
*G16H 50/70* (2018.01)
(Continued)

(52) U.S. Cl.
CPC ............ *G16H 50/30* (2018.01); *G06Q 10/06* (2013.01); *G06Q 50/24* (2013.01); *G16H 50/20* (2018.01); *G16H 50/70* (2018.01)

(58) Field of Classification Search
CPC . G06F 19/3431; G06F 19/3443; G16H 50/20; G16H 50/70
See application file for complete search history.

(56) References Cited

U.S. PATENT DOCUMENTS

| | | | |
|---|---|---|---|
| 6,059,724 A * | 5/2000 | Campell | A61B 5/7264 600/300 |
| 7,567,870 B1 * | 7/2009 | Hood | G01N 33/6803 435/6.14 |

(Continued)

FOREIGN PATENT DOCUMENTS

| | | |
|---|---|---|
| EP | 2297359 | 3/2011 |
| WO | 2012040784 A1 | 4/2012 |
| WO | WO-2012040784 A1 * | 4/2012 ........... C12Q 1/6886 |

OTHER PUBLICATIONS

International Search Report and Written Opinion of the International Searching Authority for PCT Application No. PCT/US2014/051907, dated Dec. 18, 2014, 13 pages.

(Continued)

*Primary Examiner* — Linh Giang Le
(74) *Attorney, Agent, or Firm* — Meunier Carlin & Curfman LLC (57) ABSTRACT

Methods and systems for predicting prognosis of a patient are provided. An example method can comprise determining a target set, wherein the target set comprises patient data from a target patient, determining a reference set, wherein the reference set comprises patient data from a plurality of patients, and the plurality of patients have one or more features in common with the target patient, determining common comparison features, normalizing common comparison feature data by a normalization method, weighting the normalized common comparison feature data, and determining one or more best matches by applying a classification method to the weighted normalized common compari- (Continued)

FIG. 1 son feature data. Finally, the prognosis of the patient in the target set is predicted.

15 Claims, 5 Drawing Sheets

(51) Int. Cl.
  *G16H 50/20* (2018.01)
  *G06Q 50/24* (2012.01)
  *G06Q 10/06* (2012.01)

(56) References Cited

U.S. PATENT DOCUMENTS

| | | | | |
|---|---|---|---|---|
| 2002/0138492 | A1* | 9/2002 | Kil | G06K 9/6253 |
| 2004/0265874 | A1* | 12/2004 | Binder | G01N 33/564 |
| | | | | 435/6.16 |
| 2006/0194211 | A1* | 8/2006 | Burczynski | C12Q 1/6886 |
| | | | | 435/6.14 |
| 2006/0206359 | A1* | 9/2006 | Stang | G06F 19/324 |
| | | | | 705/2 |
| 2006/0265138 | A1* | 11/2006 | Bowtell | C12Q 1/6886 |
| | | | | 702/20 |
| 2010/0332143 | A1 | 12/2010 | Onell et al. | |
| 2012/0166208 | A1 | 6/2012 | Gillam et al. | |
| 2013/0197938 | A1 | 8/2013 | Bayouk et al. | |

OTHER PUBLICATIONS

Supplementary European Search Report issued by the European Patent Office for Application No. EP 14837934, dated Mar. 22, 2017, 4 pages.

Communication Pursuant to Article 94(3) EPC issued by the European Patent Office for Application No. EP 14837934, dated Apr. 3, 2017, 9 pages.

Summons to Attend Oral Proceedings issued by the European Patent Office for Application No. EP 14837934, dated Feb. 1, 2018, 11 pages.

* cited by examiner

Step 1: *Find best patient matches using shared features*

Step 2: *Infer clinical outcomes from best matches*

Patient Evaluated:     Josh Jones
Features Used:         Tumor expression data
Parameter Desired:     Response to Doxorubicin
Reference Set          NCI-60

No. of similar matches  5
Requested

RESULTS

Summary: Given that your 5 most similar patient matches trended toward the sensitive spectrum, MatchTx predicts that Josh Jones will most likely be sensitive to doxorubicin.

FIG. 5

METHODS FOR PREDICTING PROGNOSIS

CROSS-REFERENCE TO RELATED APPLICATION

This application claims the priority of and the benefit of the filing date of U.S. Provisional Application No. 61/867,767, filed Aug. 20, 2013, which is herein incorporated in its entirety.

BACKGROUND

Treatment for cancer and other disease often involves trial and error. For example, a certain treatment may be effective for some patients, but not others. Physicians often have little knowledge on how a particular patient will respond to a certain treatment prior to the treatment. An accurate method of predicting a patient's prognosis remains elusive. There is a need to improve the accuracy of a patient's prognosis or prediction of response to therapy.

SUMMARY

It is to be understood that both the following general description and the following detailed description are exemplary and explanatory only and are not restrictive, as claimed. Provided are methods and systems for predicting the prognosis of a patient or their response to therapy. An example method can comprise determining a target set, wherein the target set comprises patient data from a target patient, determining a reference set, wherein the reference set comprises patient data from a plurality of patients, and the plurality of patients have one or more features in common with the target patient, determining common comparison features, normalizing common comparison feature data by a normalization method, weighting the normalized common comparison feature data, determining one or more best matches by applying a classification method to the weighted normalized common comparison feature data, and predicting the prognosis of the patient in the target set.

Another example method can comprise receiving a target set, wherein the target set comprises patient data from a target patient, receiving a reference set, wherein the reference set comprises patient data from a plurality of patients, and wherein the plurality of patients have at least one feature in common with the target patient, normalizing one or more features by a normalization method, weighting the one or more normalized features, applying a classifier to determine which of the plurality of patients comprises a match to the target patient based on comparison of weighted normalized one or more features of the target set with the one or more weighted normalized features of the reference set, and predicting the prognosis of the patient in the target set.

Another example method can comprise receiving patient data, wherein the patient data comprises genomic data, clinical data, or both; and classifying the patient data using a trained classifier, wherein classifying the patient data using a trained classifier can comprise presenting, to a classifier, pre-classified patient data; and determining, by the classifier, an optimal feature vector for the pre-classified patient data from a set of comparison features.

The method disclosed herein can take into account of differences between patients and more than one type of patient data. The method can provide an extensible platform for prognosis prediction to guide treatment decisions. The method can be used by a physician to determine which treatments can work for a particular patient and what the patient's prognosis can be. The method can be performed iteratively. For example, the method can make predictions for a plurality of drug treatments for a patient and rank them.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Figure 1:
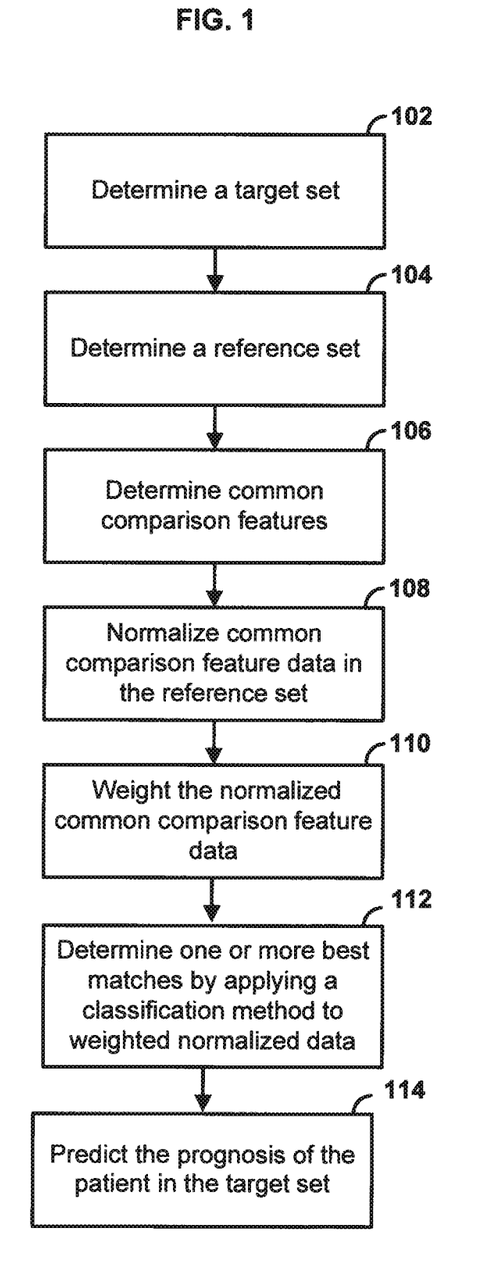
FIG. 1 is a flowchart illustrating an example method for predicting prognosis.

FIG. 1 is a flowchart illustrating an example method for predicting prognosis. At step 102, a target set can be determined. In an aspect, the target set can comprise patient data from a target patient. For example, the target set can comprise data for a patient with a disease or physical trait who needs a prognosis prediction for response to a certain drug treatment. In an aspect, the data can comprise genomic data, clinical data, or both. As an example, the genomic data can comprise tumor gene expression profile data, data on single nucleotide variation obtained from next generation sequencing, single nucleotide polymorphism data, mutational data (missense mutations, nonsense mutations, silent mutations), gene rearrangements (i.e., gene fusion proteins), gene amplifications, gene deletions, transcript variants, copy number variations, methylation variations, and the like. As another example, the target set can comprise patient data related to a disease type, a physical trait, a drug treatment, (effective clinical dose, time to next treatment, progression-free survival on the drug, overall survival) and the like. These genomic mutational data can be the generated from in-house DNA/RNA sequencing and/or commercially available genomic testing platforms. In an aspect, patient data can comprise presence or absence of medications, dosage of medications, amount of exercise per day, amount of fruit and/or vegetables consumed, physical traits (e.g., height, weight, body mass index, blood pressure, resting heart rate), clinical lab test data (e.g., total cholesterol, prostate specific antigen, hemoglobin), tumor pathologic characteristics (e.g., grade, stage, immunohistochemistry staining status, breakpoint mutations by fluorescence in situ hybridization or other molecular techniques).

At step 104, a reference set can be determined. The reference set can comprise data reflecting prior diagnosis of one or more patients. In an aspect, the reference set can be determined from the aggregation of clinical, genomic, drug data, combinations thereof, and the like. Exemplary data repositories can comprise one or more of: (1) publically available sources; (2) data collected by sponsor institutions during the course of a clinical trial; (3) data collected by third party genomic profiling agencies; (4) data collected by medical institutions as a part of a larger biobanking initiative; and (5) data collected by third party organizations as part of a larger biobanking initiative. In an aspect, the method automatically compares similar data with similar data, so that expanded data collection is not problematic. As another example, the reference set can be determined using DNA sequencing data performed as part of (1) retrospective chart review, (2) prospective clinical trials, and/or (3) larger biobanking initiatives. In an aspect, the reference set can comprise patient data from a plurality of patients, wherein the plurality of patients have at least one feature in common with the target patient. As an example, the common feature can comprise a disease, a drug treatment, a physical trait, and the like. As an example, the data in the reference set can comprise genomic data, clinical data, or both. As an example, the genomic data can comprise tumor gene expression profile data, data on single nucleotide variation obtained from next generation sequencing, single nucleotide polymorphism data, mutational data, and the like. In an aspect, the more data in the reference set, the better prognosis can be predicted.

At step 106, one or more common comparison features can be determined. In an aspect, the one or more comparison features can be common genomic and/or clinical data between the target set and the reference set. As an example, the one or more common comparison features can comprise tumor gene expression profile data, data on single nucleotide variations obtained from next generation sequencing, single nucleotide polymorphism data, mutational data, clinical data, etc. As another example, the one or more common comparison features can be related to a disease type, a physical trait, a drug treatment, and the like. In an aspect, patient data can comprise presence or absence of medications, dosage of medications, amount of exercise per day, amount of fruit and/or vegetables consumed, physical traits (e.g., height, weight, body mass index, blood pressure, resting heart rate), clinical lab test data (e.g., total cholesterol, prostate specific antigen, hemoglobin), tumor pathologic characteristics (e.g., grade, stage, immunohistochemistry staining status, breakpoint mutations by fluorescence in situ hybridization or other molecular techniques).

At step 108, common comparison feature data can be normalized by a normalization method. For example, if there are 2 patients, one with data points A through Z and another with data points C through Z (lacking points A and B), the normalization algorithm first checks for the existence of similar features. Missing data cannot be evaluated and is thus excluded from similarity comparison. Next for transcriptomic data, features can be first ranked based on their gene expression values or by their count data if RNA-seq. This rank-based normalization provides greater platform independence. Another variation can comprise quantile normalization. When processing DNA mutational data, data can be normalized to a common vocabulary. Mutational changes can be categorized into component types (e.g., missense, nonsense, silent, translocation, etc.) and the mutation designation can be normalized to the gene itself. Mutations can either be aggregated at the gene level (any gene mutation), at a specific gene position (i.e. $10^{th}$ nucleotide in the gene), at a designated region of the gene (i.e. the third exon of the gene), or at an arbitrary region of the gene (the 1000 kb around the 3' terminus). In an aspect, data normalization can improve signal-to-noise ratio. In an aspect, the normalization method can comprise functional analysis of individual microarray expression (FAIME), global normalization, lowess normalization, trimmed mean method (TMM), quantile normalization, scaling normalization, variance stabilization, invariant method, and the like. As an example, if the data in common comparison features are genomic in nature, functional analysis of individual microarray expression (FAIME) can be used to normalize the data and a pathway score can be calculated. In an aspect, a method of calculating pathway scores in the transcriptomic space can comprise taking a sum of gene expression values for a set of genes of interest, assuming that an appropriate normalization scheme was followed. As another example, a pathway score in the DNA/RNA mutational space can be determined by counting a number of gene-associated variations within a set of genes. This can also be weighted such that functional gene changes (i.e. missense or nonsense mutations in the exon) are weighted more than intronic silent mutations. The pathway score can provide a more consistent and stable platform for comparing the target set and the reference set. In an aspect, a sequenced approach can be applied in normalizing common comparison feature data. For example, when the patient data in the reference set comprise both genomic data and clinical data, the genomic data can be normalized prior to normalizing the clinical data.

At step 110, the normalized common comparison feature data can be weighted. For example, the weighting can evaluate the relative importance of each of the common comparison features by estimating the information gain associated with each feature. In an aspect, a weight number can be assigned to each common comparison feature. As an example, the weighting performed can be a function of outcome (phenotypic) data being measured. In the case of drug sensitivity in cell lines where the outcomes variable is an inhibitory concentration 50 (IC50), weighting can be performed by evaluating the reference set and comparing individuals with a high IC50 versus those with a low IC50. The significance of a difference as measured by standard statistical measures provides the weight of each of the features. When approaching outcomes based data (e.g., progression free survival, overall survival, or a temporal endpoint), the weighting can be performed per feature by using the absolute value of the hazard ratio based on a Cox regression analysis. The weighting can take into account the features that are not independent and avoid over or under weighting of certain comparison features. In an aspect, a sequenced approach can be applied in the weighting common comparison feature data. For example, when the patient data in the reference set comprise both genomic data, and clinical data, the genomic data can be weighted prior to weighting of the clinical data. In an aspect, highly important features in the genomic data can be correlated with one or more phenotypic features. Phenotypic features that are subsumed or explained by the genomic data can then be eliminated from comparison. This can reduce redundancy and overweighting of highly correlated features.

In an aspect, the weighting method can comprise ridge regression with cross validation, elastic-net regression with cross validation, RELIEFF, weighting based on the log(p-value) of observed correlation between common comparison features, weighting based on observed correlations between common comparison features with adjustment for false-discovery, and the like.

As an example, the weighting method based on observed correlations between common comparison features with adjustment for false-discovery can comprise randomly selecting common comparison features and building a linear predictive model for the selected features, calculating the information change associated with adding or removing for each selected feature. Adjustments can be made to the observed rank-ordered information changes against the expected rank-ordered information changes using a null model (e.g., false discovery adjustment). Based on the adjusted changes in information, a probability weight for adding or removing each feature can be generated. The process can be repeated until the probability weights stabilize.

At step 112, one or more best matches can be determined by applying a classification method to the weighted normalized common comparison feature data. In an aspect, the classification method can be selected from among a k-Nearest Neighbors (K-NN) classification method, a linear discriminant classification method, a quadratic discriminant classification method, a support vector machine classification method, and the like. As an example, the best matches can be calculated using K-nearest neighbor method. The best matches can be identified by a K-NN score. In an aspect, the K-NN method is a weighted K-NN based on the calculated feature weights. For example, the higher the K-NN score, the closer the match between a reference patient and the target patient.

At step 114, the prognosis of the patient in the target set can be predicted. For example, the best matches in the reference can be used to predict the prognosis of the patient in the target set. Specifically, if one or more best matched patients in the reference set are sensitive to a specific drug treatment, the patient in the target set can be sensitive to the drug treatment.

In an aspect, cell line data can be used in the target set and/or the reference set. For example, cell line data can comprise genotype and phenotype data to characterize cell lines. In an aspect, genotype data can comprise mRNA profiling, DNA sequencing, protein data. In another aspect, phenotype data can comprise data related to patient's response to drug treatment. As an example, cell line data can comprise National Cancer Institute 60 (NCI-60) cancer cell lines data, Broad/Novartis Cancer Cell Line Encyclopedia data, and Wellcome Trust Genomics of Drug Sensitivity data in Cancer project. Specifically, NCI-60 data can be used for drug screening for over 100,000 compounds. As an example, Doxorubicin is a major chemotherapeutic agent in the treatment of liposarcoma. However, only a small portion of patients respond to Doxorubicin treatment. The disclosed method can use the available cell lines data (e.g. NCI-60 cell lines) to predict whether a patient with liposarcoma can respond to Doxorubicin treatment. Specifically, liposarcoma cell line data (e.g., gene expression data) for a patient can be used as a target set, and the NCI-60 cell data (e.g., gene expression data) can be used as a reference set. Genomic data and Doxorubicin treatment sensitivities are well-established for NCI-60 cell lines and thus can constitute a useful reference set. NCI-60 comprises 60 human cancer cell lines derived from nine diverse tissues, which do not include sarcoma. As an example, NCI-60 genomic data can be normalized by one or more normalization method (e.g., FAIME), generating molecular pathway scores. Then a weighting method can be applied to the normalized data (e.g., molecular pathway scores), and a classification method (e.g., K-nearest neighbor (K-NN) method) can be used to calculate the best match between the target set and the reference set. By examining the best matches, a prognosis of Doxorubicin treatment for the patient in the target set can be obtained.

Figure 2:
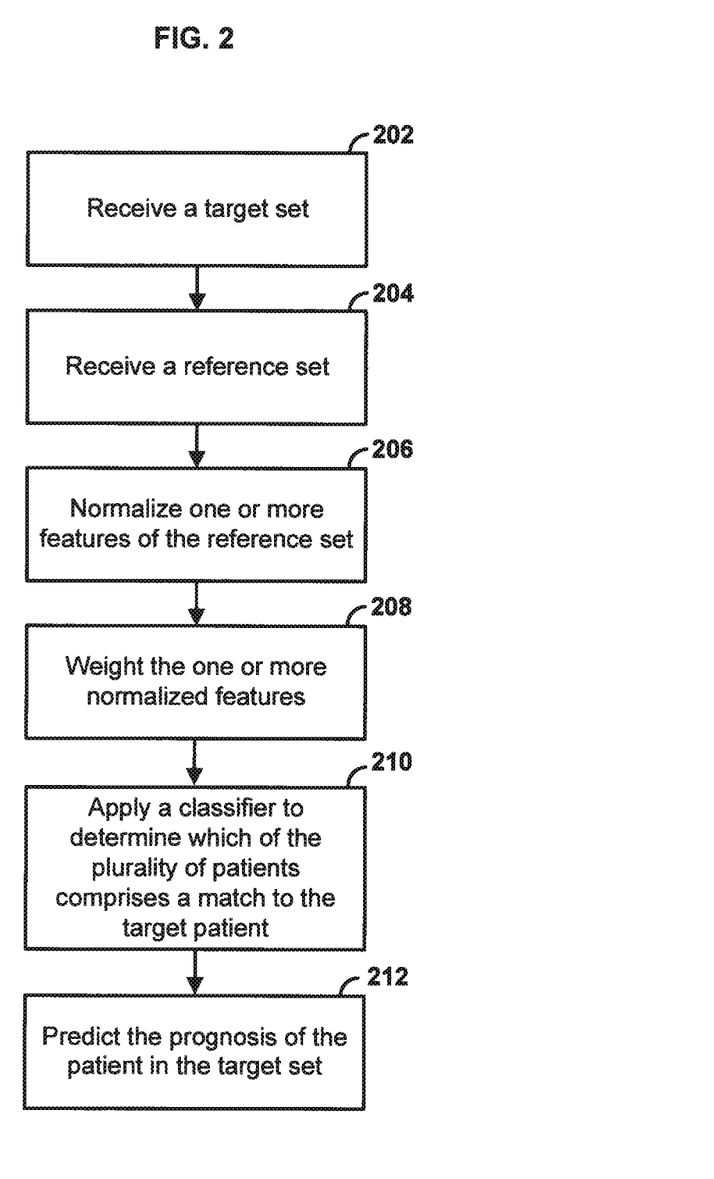
FIG. 2 is a flowchart illustrating another example method for predicting prognosis.

FIG. 2 is a flowchart illustrating another example method for predicting prognosis. At step 202, a target set can be received. In an aspect, the target set can be received from patients after their tissue of interest has been tested by one or more of: third party data purveyors, academic medical center Clinical Laboratory Improvement Amendments (CLIA) certified sequencing facilities, or genomic sequencing centers performing tests for research purposes. In an aspect, the target set can be provided by direct digital feed, in the form of an electronic report that can be downloaded and provided to the system, or other similar methods. In an aspect, the target set can comprise patient data from a target patient. In an aspect, the target set can be received by a computer. As an example, the target set can comprise data of a patient with a certain disease or physical trait who is in need of prognosis prediction in response to a certain drug treatment. As an example, the patient data can comprise tumor gene expression profile data, data on single nucleotide variations obtained from next generation sequencing data, single nucleotide polymorphism data, mutational data, clinical lab data, and the like. As another example, the patient data can be related to a disease type, a physical trait, a drug treatment, and the like.

At step 204, a reference set can be received. In an aspect, the reference can be received from the aggregation of clinical, genomic, and drug data from one or more of: (1) publically available sources; (2) data collected by sponsor institutions during the course of a clinical trial; (3) data collected by third party genomic profiling agencies; (4) data that is collected by medical institutions as a part of a larger biobanking initiative; and (5) data collected by third party organizations as part of a larger biobanking initiative. All users have access to publically available data. Hospital acquired and third party data are available based on licensing agreements. In an aspect, the reference set can be received by a computer. The reference set can comprise patient data from a plurality of patients, and the plurality of patients can have at least one feature in common with the target patient. As an example, the patient data can comprise tumor gene expression profile data, data on single nucleotide variations obtained from next generation sequencing, single nucleotide polymorphism data, mutational data, clinical data, etc. As another example, the patient data can be related to a disease type, a physical trait, a drug treatment associated with the patient in the reference set.

At step 206, one or more features can be normalized by a normalization method. One or more features of the reference set can be normalized by a computer. As an example, normalization method can comprise functional analysis of individual microarray expression (FAIME), global normalization, lowess normalization, trimmed mean method (TMM), quantile normalization, scaling normalization, variance stabilization, invariant method, and the like. In an aspect, normalizing common comparison feature data can improve signal to noise ratio. As an example, if the data in common comparison features are genomic in nature, functional analysis of individual microarray expression (FAIME) can be used to normalize the data. A pathway score can be calculated after normalization. The pathway score can provide a more consistent and stable platform for comparing the target set and the reference set. In an aspect, a sequenced approach can be applied in normalizing common comparison feature data. For example, when the patient data in the reference set comprise both genomic data and clinical data, the genomic data can be normalized prior to normalizing the clinical data.

At step 208, one or more normalized features can be weighted. In an aspect, weighting can provide more accurate and robust weights to find best matches. In an aspect, the weighting can evaluate the relative importance of the common comparison features by estimating the information gain associated with each feature. For example, the weighting can assign weights to one or more normalized features to reflect the importance of the respective features. In another aspect, the weighting can take into account the features that are not independent and avoid over or under weighting of certain comparison features. In an aspect, weighting can reflect a physician's view on the importance of the specific comparison feature. In an aspect, a sequenced approach can be applied in weighting common comparison feature data. For example, when the patient data in the reference set comprise both genomic data and clinical data, the genomic data can be weighted prior to weighting the clinical data.

At step 210, a classifier can be applied to determine which of the plurality of patients comprises a match to the target patient based on a comparison of one or more features of the target set with the one or more weighted normalized features of the reference set. In an aspect, the classifier can be selected from among a k-Nearest Neighbors classifier, a linear discriminant classifier, a quadratic discriminant classifier, a support vector machine classifier, and the like. As a specific example, a classifier can be applied to classify whether a patient is sensitive or resistant to a drug treatment. A classifier (e.g., K-nearest neighbor classification method) can identify one or more best matches (e.g., nearest neighbors) between the target set and the reference set, and determine how the identified best matches (e.g., nearest neighbors) can respond to a drug treatment (e.g., sensitive or resistant to a drug treatment). As a result, the response to the drug treatment in the target set can be determined.

At step 212, the prognosis of the target patient can be predicted. For example, one or more best matches in the reference set can be used to predict the prognosis of the target patient. Specifically, if one or more best matched patients in the reference set are sensitive to a specific drug treatment, the patient in the target set can be sensitive to the drug treatment.

Figure 3:
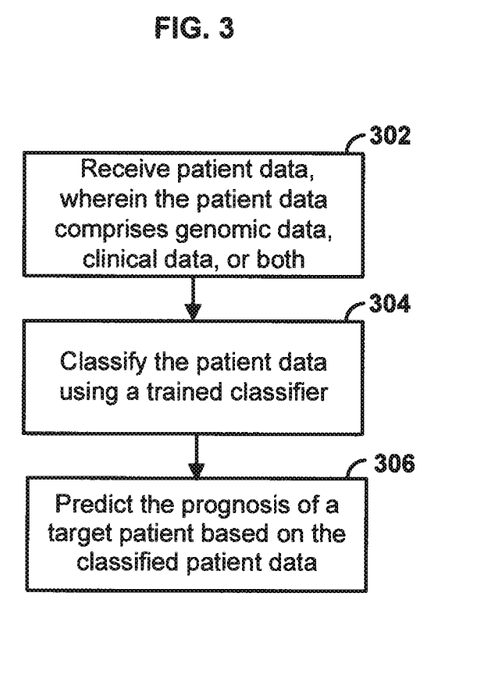
FIG. 3 is a flowchart illustrating another example method for predicting prognosis.

FIG. 3 is a flowchart illustrating another example method for predicting prognosis. At step 302, patient data can be received, wherein the patient data can comprise genomic data, clinical data, or both. In an aspect, patient data can be received by a computer. In an aspect, the patient data can be received from patients after their tissue of interest has been tested by one or more of: third party data purveyors, academic medical center Clinical Laboratory Improvement Amendments (CLIA) certified sequencing facilities, or genomic sequencing centers performing tests for research purposes. In an aspect, the target set can be provided by direct digital feed, in the form of an electronic report that can be downloaded and fed into the system, or other similar methods. As an example, the patient data can comprise cell line data. As an example, the genomic data can comprise tumor gene expression profile data, data on single nucleotide variations obtained from next generation sequencing, single nucleotide polymorphism data, mutational data, and the like. In an aspect, the clinical data can comprise clinical lab data such as blood sample data and urine sample data. In an aspect, the patient data can be related to a disease type, a physical trait, a drug treatment, and the like. As an example, patient data can comprise presence or absence of medications, dosage of medications, amount of exercise per day, amount of fruit and/or vegetables consumed, physical traits (e.g., height, weight, body mass index, blood pressure, resting heart rate), clinical lab test data (e.g., total cholesterol, prostate specific antigen, hemoglobin), tumor pathologic characteristics (e.g., grade, stage, immunohistochemistry staining status, breakpoint mutations by fluorescence in situ hybridization or other molecular techniques).

At step 304, the patient data can be classified using a trained classifier. In an aspect, classifying can comprise processing a reference set such that features of interest have a weight prior to the actual classification step with the target data, and classifying the target data based on the weighted reference set. In an aspect, classifying the patient data using a trained classifier can comprise presenting pre-classified patient data to a classifier, and determining, by the classifier, one or more feature vectors for the pre-classified patient data from a set of comparison features. In an aspect, a first determined feature vector provides maximal ability to discriminate between phenotypes of interest. Additional feature vectors with a lower ability to discriminate between phenotypes can be used in addition to or in place of the first determined feature vector. When multiple feature vectors are used, the vectors are weighted based on their ability to discriminate between phenotypes. In an aspect, the pre-classified patient data can be normalized and weighted before using a trained classifier. As an example, the classifier can be one or more of a k-Nearest Neighbors (K-NN) classifier, a linear discriminant classifier, a quadratic discriminant classifier, a support vector machine, and the like. In an aspect, the optimal feature vector can be determined using a trained classifier on the weighted normalized reference patient data, and thus one or more best matches between a target patient and one or more of the plurality of patients can be identified. Best matches are determined based on identifying reference set patients that are in the top K-NN quartile presented to the user with the K-NN scores normalized to the score of the target patient to themself.

At step 306, the prognosis of a target patient can be predicted based on the classified patient data. For example, one or more best matches in the reference patient data can be used to predict the prognosis of the target patient. Specifically, if one or more best matched patients are sensitive to a specific drug treatment, the target patient can be sensitive to the drug treatment.

In an aspect, a sequenced approach can be applied in classifying the patient data. For example, when the patient data comprise both genomic data and clinical data, the genomic data can be classified using a first trained classifier prior to classifying the clinical data using a second trained classifier. In an aspect, the first trained classifier can be different from the second trained classifier.

Figure 4:
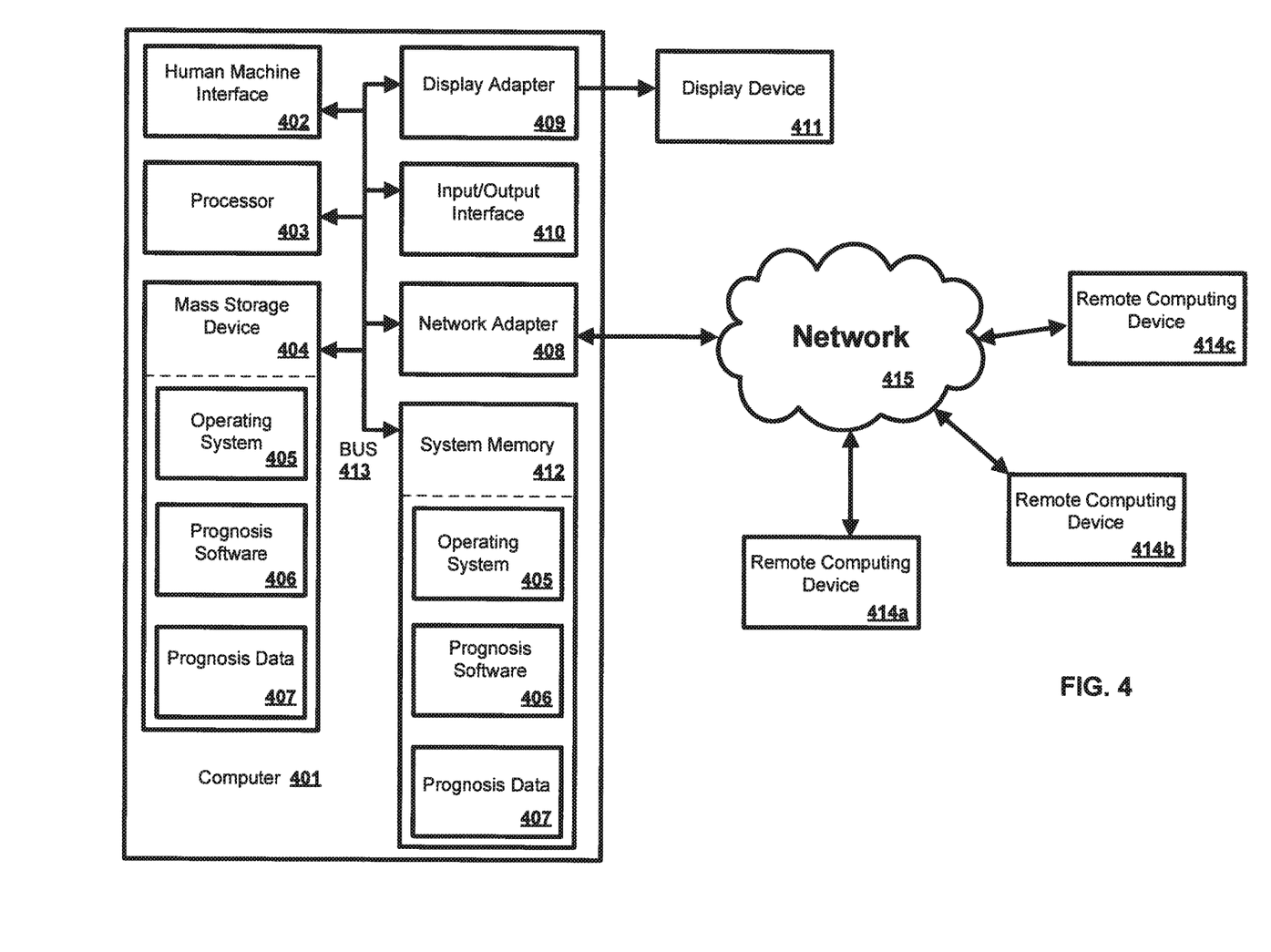
FIG. 4 is a block diagram illustrating an example computing device in which the present systems and methods can operate.

In an exemplary aspect, the methods and systems can be implemented on a computer 401 as illustrated in FIG. 4 and described below. Similarly, the methods and systems disclosed can utilize one or more computers to perform one or more functions in one or more locations. Computer 401 can be configured to receive target patient data, wherein the target patient data comprises genomic data and clinical data from a target patient, receiving a plurality of patient data, wherein the plurality of patient data comprises genomic data and clinical data from a plurality of patients, normalizing one or more features of the genomic data contained in the plurality of patient data, weighting the one or more normalized features of the genomic data contained in the plurality of patient data, and applying a classifier to the target patient data and the plurality of patient data to determine a match between the target patient and one of the plurality of patients. Computer 401 can also display match outcome.

FIG. 4 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 401. The components of the computer 401 can comprise, but are not limited to, one or more processors or processing units 403, a system memory 412, and a system bus 413 that couples various system components including the processor 403 to the system memory 412. In the case of multiple processing units 403, the system can utilize parallel computing.

The system bus 413 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI) bus, a PCI-Express bus, a Personal Computer Memory Card Industry Association (PCMCIA) bus, Universal Serial Bus (USB) and the like. The bus 413, and all buses specified in this description can also be implemented over a wired or wireless network connection and each of the subsystems, including the processor 403, a mass storage device 404, an operating system 405, prognosis software 406, prognosis data 407, a network adapter 408, system memory 412, an Input/Output Interface 410, a display adapter 409, a display device 411, and a human machine interface 402, can be contained within one or more remote computing devices 414a,b,c at physically separate locations, connected through buses of this form, in effect implementing a fully distributed system.

The computer 401 typically comprises a variety of computer readable media. Exemplary readable media can be any available media that is accessible by the computer 401 and comprises, for example and not meant to be limiting, both volatile and non-volatile media, removable and non-removable media. The system memory 412 comprises computer readable media in the form of volatile memory, such as random access memory (RAM), and/or non-volatile memory, such as read only memory (ROM). The system memory 412 typically contains data such as prognosis data 407 and/or program modules such as operating system 405 and prognosis software 406 that are immediately accessible to and/or are presently operated on by the processing unit 403.

In another aspect, the computer 401 can also comprise other removable/non-removable, volatile/non-volatile computer storage media. By way of example, FIG. 4 illustrates a mass storage device 404 which can provide non-volatile storage of computer code, computer readable instructions, data structures, program modules, and other data for the computer 401. For example and not meant to be limiting, a mass storage device 404 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 404, including by way of example, an operating system 405 and prognosis software 406. Each of the operating system 405 and prognosis software 406 (or some combination thereof) can comprise elements of the programming and the prognosis software 406. Prognosis data 407 can also be stored on the mass storage device 404. Prognosis data 407 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 401 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit 403 via a human machine interface 402 that is coupled to the system bus 413, but can be connected by other interface and bus structures, such as a parallel port, game port, an IEEE 1394 Port (also known as a Firewire port), a serial port, or a universal serial bus (USB).

In yet another aspect, a display device 411 can also be connected to the system bus 413 via an interface, such as a display adapter 409. It is contemplated that the computer 401 can have more than one display adapter 409 and the computer 401 can have more than one display device 411. For example, a display device can be a monitor, an LCD (Liquid Crystal Display), or a projector. In addition to the display device 411, other output peripheral devices can comprise components such as speakers (not shown) and a printer (not shown) which can be connected to the computer 401 via Input/Output Interface 410. Any step and/or result of the methods can be output in any form to an output device. Such output can be any form of visual representation, including, but not limited to, textual, graphical, animation, audio, tactile, and the like. The display 411 and computer 401 can be part of one device, or separate devices.

The computer 401 can operate in a networked environment using logical connections to one or more remote computing devices 414a,b,c. By way of example, a remote computing device can be a personal computer, portable computer, smartphone, a server, a router, a network computer, a peer device or other common network node, and so on. Logical connections between the computer 401 and a remote computing device 414a,b,c can be made via a network 415, such as a local area network (LAN) and/or a general wide area network (WAN). Such network connections can be through a network adapter 408. A network adapter 408 can be implemented in both wired and wireless environments. Such networking environments are conventional and commonplace in dwellings, offices, enterprise-wide computer networks, intranets, and the Internet.

For purposes of illustration, application programs and other executable program components such as the operating system 405 are illustrated herein as discrete blocks, although it is recognized that such programs and components reside at various times in different storage components of the computing device 401, and are executed by the data processor(s) of the computer. An implementation of prognosis software 406 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

Figure 5:
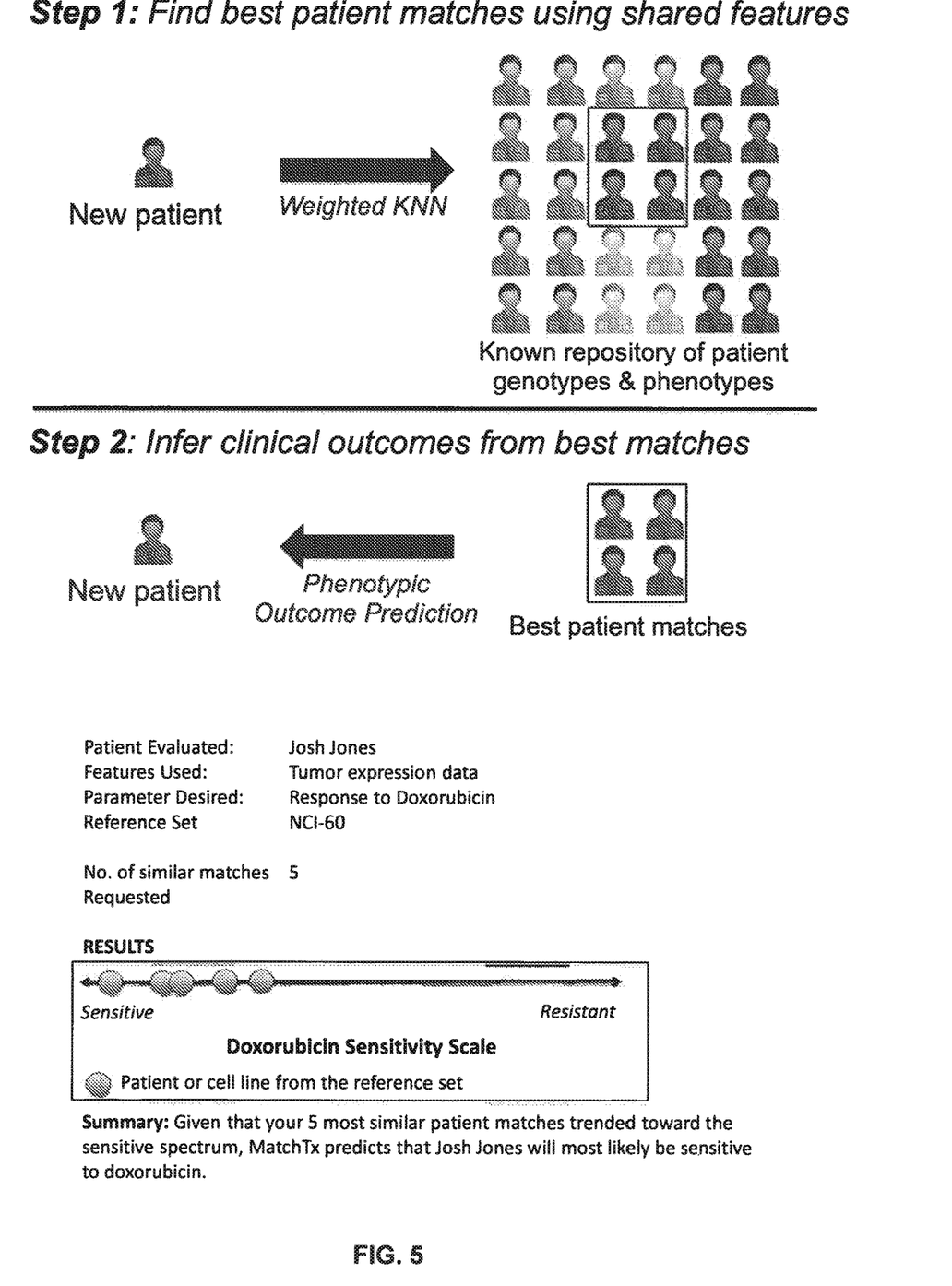
FIG. 5 is a diagram illustrating an example method for predicting prognosis.

FIG. 5 is a diagram illustrating an example method for predicting prognosis. As an example, a new patient (target patient) is in need of prognosis prediction for the response to a specific drug treatment (e.g., Doxorubicin treatment). In an aspect, a target set can be determined by the available genomic and clinical information. In an aspect, the reference set can be determined by what genomic testing has been performed on the patient. For example, if the patient has undergone an in-depth genomic analysis of the tissue in question, a larger reference set can be determined, which can in turn provide a higher yield analysis. In an aspect, the reference set can comprise patient data (e.g., NCI-60) from a plurality of patients. The plurality of patients can have one or more features in common with the target patient. Then common comparison features can be determined (e.g., specific tumor expression data). The common comparison feature data can be normalized by a normalization method, the normalized common comparison feature data can be weighted, and one or more best matches can be determined by applying a classification method to the weighted normalized common comparison feature data. Best matches can be determined based on identifying reference set patients that are in the top K-NN quartile presented to the user with the K-NN scores normalized to the score of the target patient to themselves. As an example, five best matches can be found. One or more best matches can be used to predict the prognosis of the patient to the drug treatment. Specifically, if five matched patients are sensitive to the specific drug treatment (e.g. Doxorubicin treatment), the new patient (target patient) can be sensitive to the drug treatment (e.g. Doxorubicin treatment). In an aspect, the method can be performed iteratively. For example, the method can generate predictions for any number of drug treatments. The sensitivity of the drug treatments for a target patient can be ranked according to the sensitivity of best matches to the specific drug in the reference set.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for predicting the prognosis of a patient to a drug treatment comprising:
   determining, using a computer, a target set, wherein the target set comprises patient data from a target patient;
   determining, using the computer, a reference set, wherein the reference set comprises patient data from a plurality of patients, wherein the plurality of patients have one or more features in common with the target patient;
   determining, using the computer, common comparison feature data, wherein the common comparison feature data comprises common genomic mutational data, common clinical data, and a common disease type between the target set and the reference set;
   normalizing, using the computer, the common comparison feature data by a normalization method;
   weighting, using the computer, the normalized common comparison feature data;
   determining, using the computer, a plurality of best matched patients in the reference set by applying a classification method to the weighted normalized common comparison feature data, wherein the plurality of best matched patients in the reference set are sensitive to a specific drug treatment;
   returning, using the computer, the plurality of best matched patients in the reference set; and
   predicting, using the computer, that the target patient in the target set is sensitive to the specific drug treatment based on the sensitivity of the plurality of best matched patients in the reference set to the specific drug treatment, wherein the patient data comprises genomic data and clinical data.

2. The method of claim 1, wherein the common comparison features further comprise cell line data.

3. The method of claim 1, wherein the normalization method comprises functional analysis of individual microarray expression (FAIME), global normalization, lowess normalization, trimmed mean method (TMM), quantile normalization, scaling normalization, variance stabilization, or invariant method.

4. The method of claim 1, wherein weighting the normalized common comparison feature data comprises identifying non-independent data.

5. The method of claim 1, wherein patient data comprise both genomic data and clinical data, and wherein the common genomic mutational data is normalized and weighted prior to normalizing and weighting the common clinical data and the common disease type.

6. The method of claim 1, wherein the classification method is selected from a group consisting of:
a k-Nearest Neighbors classification method;
a linear discriminant classification method;
a quadratic discriminant classification method; and
a support vector machine classification method.

7. A method for predicting the prognosis of a patient to a drug treatment, comprising:
receiving, at a computer, a target set, wherein the target set comprises patient data from a target patient;
receiving, at the computer, a reference set, wherein the reference set comprises patient data from a plurality of patients, and wherein the plurality of patients have at least one feature in common with the target patient, wherein the at least one feature in common comprises common genomic mutational data, common clinical data, and a common disease type between the target set and the reference set;
normalizing, using the computer, one or more features of the reference set,
weighting, using the computer, the one or more normalized features;
applying, using the computer, a classifier to determine which of the plurality of patients in the reference set are a best match to the target patient based on a comparison of one or more features of the target set with the one or more weighted normalized features of the reference set, wherein the plurality of patients in the reference set that are the best match to the target patient are sensitive to a specific drug treatment;
returning, using the computer, the plurality of patients in the reference set that are the best match to the target patient; and
predicting, using the computer, that the target patient is sensitive to the specific drug treatment based on the sensitivity of the plurality of patients in the reference set that are the best match to the target patient to the specific drug treatment, wherein the patient data comprises genomic data and clinical data.

8. The method of claim 7, wherein the at least one feature in common further comprises one or more of, a disease, a drug treatment, and a physical trait.

9. The method of claim 1, wherein returning, using the computer, the plurality of best matched patients in the reference set comprises displaying the plurality of best matched patients in the reference set on a display of the computer.

10. The method of claim 7, wherein returning, using the computer, the plurality of patients in the reference set that are the best match to the target patient comprises displaying the plurality of patients in the reference set that are the best match to the target patient on a display of the computer.

11. The method of claim 1, further comprising returning, using the computer, a rank-ordered list of predictive features from the weighted normalized common comparison feature data.

12. The method of claim 11, wherein returning, using the computer, the rank-ordered list of predictive features from the weighted normalized common comparison feature data comprises displaying the rank-ordered list of predictive features from the weighted normalized common comparison feature data on a display of the computer.

13. The method of claim 1, wherein the weighted normalized common comparison feature data further comprises genomic data including a combination of two or more of gene expression profile data, data on single nucleotide variation, single nucleotide polymorphism data, gene rearrangements, gene amplifications, gene deletions, transcript variants, copy number variations, and methylation variations.

14. The method of claim 1, wherein the common comparison feature data comprises a combination of the common genomic mutational data, the common clinical data and the common disease type.

15. The method of claim 5, wherein the common comparison feature data is normalized and weighted prior to applying the classification method.

* * * * *